United States Patent
Cowan

(10) Patent No.: US 6,586,614 B2
(45) Date of Patent: Jul. 1, 2003

(54) PRODUCTION OF AROMATIC PHOSPHITES

(75) Inventor: Justin Mark Cowan, Worcester (GB)

(73) Assignee: Rhodia Consumer Specialties Limited, Oldbury (GB)

( * ) Notice: Subject to any disclaimer, the term of this patent is extended or adjusted under 35 U.S.C. 154(b) by 0 days.

(21) Appl. No.: 10/081,832

(22) Filed: Feb. 22, 2002

(65) Prior Publication Data
US 2002/0120162 A1 Aug. 29, 2002

(30) Foreign Application Priority Data
Feb. 27, 2001 (GB) .............................. 0104778

(51) Int. Cl.[7] .................................. C07F 9/142
(52) U.S. Cl. ........................................ 558/97
(58) Field of Search ............................ 558/97

(56) References Cited

U.S. PATENT DOCUMENTS

| 4,089,884 A | 5/1978 | Shinohara et al. |
| 4,218,405 A | 8/1980 | Turley |
| 5,710,307 A | 1/1998 | Ohlendorf et al. |

Primary Examiner—Joseph K. McKane
Assistant Examiner—Kamal Saeed
(74) Attorney, Agent, or Firm—Frishauf, Holtz, Goodman & Chick, P.C.

(57) ABSTRACT

A method for the production of an aromatic phosphite by reacting an aromatic hydroxy-compound with a phosphorus trihalide in the presence of a tertiary amine and a non-protic solvent, said solvent being mobile below −20° C. Suitable tertiary amines include tri-propyl amines, tri-butyl amines, tri-n-propylamine, tri-iso-propylamine, tri-n-butylamine, tri-iso-butylamine and tri-t-butylamine.

9 Claims, No Drawings

PRODUCTION OF AROMATIC PHOSPHITES

This invention relates to the production of aromatic phosphites and in particular to an improved method for the production of aromatic phosphites, as well as to aromatic phosphites produced thereby.

Aromatic phosphites are useful intermediates in the formation of dicarboxylic acid derivatives such as adiponitrile. Hitherto, the phosphite has been obtained by reacting phosphorus trichloride ($PCl_3$) and an aromatic hydroxy compound, in the presence of a solvent such as toluene and an alkyl amine such as triethylamine, to remove hydrogen chloride from the reaction. This reaction is carried out at low temperature, generally at about $-20°$ C. or less.

When triethylamine is added to the above reaction mixture, it precipitates out of solution as the hydrochloride and forms a thick slurry which can coat the sides of reaction vessels and impede the manufacturing process. The precipitation is exacerbated when the production is scaled-up, making the slurry impossible to stir adequately without the use of special equipment such as a multiple impeller.

The applicants have devised an improved process in which the disadvantages of the hitherto-used method are minimised.

Accordingly, the present invention provides an improved method for the production of an aromatic phosphite from an aromatic hydroxy-compound and a phosphorus trihalide in the presence of a tertiary amine and a non-protic solvent which is mobile below $-20°$ C., wherein the improvement comprises the use, as said tertiary amine, of a tri-propyl or a tributyl amine.

The present invention also provides an aromatic phosphite made by the improved method described in the immediately-preceding paragraph.

The tertiary amine may be tri-n-propylamine, tri-iso-propylamine, tri-n-butylamine, tri-iso-butylamine, or tri-t-butylamine.

The phosphorus trihalide may be phosphorus trichloride or phosphorus tribromide. Preferably the phosphorus trihalide is phosphorus trichloride.

The aromatic hydroxy-compound may be a substituted or unsubstituted aromatic mono-or polyhydric alcohol, for example a substituted phenol (e.g. thymol) or an unsubstituted phenol, or a substituted or unsubstituted diphenol, resorcinol or quinone. Alternatively, the aromatic hydroxy-compound may have a condensed ring system and may be, for example, a substituted or unsubstituted monohydric or polyhydric naphthol, anthrol or phenanthrol.

The solvent may be, for example, an aromatic compound such as toluene, xylene, monochlorobenzene, dichlorobenzene, or 1, 4, 5-trimethyl benzene.

Preferably the solvent is used in the minimum amount to maintain the reaction in a mobile phase.

A preferred embodiment of the invention will now be illustrated, merely by way of example, as follows.

EXAMPLE 1

Toluene (610 g) was charged to a 1-liter reactor fitted with a distillation apparatus, a 4-blade turbine stirrer and a thermometer. Thymol (0.52 moles) was charged to the reactor and the reaction mixture taken to reflux (~116° C.). 100 g of toluene was distilled out to dry the system. The reaction mixture was cooled to $-5$ to $-10°$ C. Phosphorus trichloride (0.26 moles) was added in one portion. Tripropylamine (0.79 moles) was added over 2 hours maintaining the temperature of the reaction mixture at $-5°$ C. to $-10°$ C. The tri-propylamine addition caused fuming in the headspace for the first 10% of the addition. The reaction remained a clear, pale yellow mixture (a very fine slurry) and remained readily stirrable throughout the addition. There was no observable coating of the reactor walls by the reaction mixture, This chemistry has been scaled-up to a 50-Gallon reactor using process equipment with and without an external heat exchanger. The reactor was fitted with a 3-pronged (crowfoot) impeller. The process has been shown to work successfully, both with (example 3) and without (example 2) the use of an external heat exchanger.

EXAMPLE 2

Thymol (102 moles) was charged to a 50-Gallon glass-lined reactor. Toluene (130 kg) was charged and the reaction mixture taken to reflux. 30 kg of toluene was distilled out to dry the system. The reaction mixture was cooled to $-5°$ C. to $-10°$ C. by use of refrigerated glycol connected to the reactor jacket. The refrigeration unit was rated at 5 kilowatt and this achieved an actual coolant temperature in the reactor jacket of $-17.5°$ C. Phosphorus trichloride (50.9 moles) was added in less than 5 minutes. Tripropylamine (156 moles) was added over 2.7 hrs, which maintained the reaction mixture in the temperature range of $-6°$ C. to $-11°$ C. The mixture remained readily stirrable throughout the addition. There was no observable coating of the reactor walls by the reaction mixture.

This was repeated a further two times without any observable or detrimental interference with regards to stirring.

EXAMPLE 3

Toluene (100 kg) was charged to a 50-Gallon glass-lined reactor. Melted thymol (100 moles) was then charged. A further 20 kg toluene was then added to flush through any residual thymol left in the charging line. This gave a total of 120 kg toluene. The reaction mixture was heated to reflux and 20 kg distilled out to dry the system. The reaction mixture was cooled to $-5°$ C. to $-10°$ C. by use of a fitted 2.24 $m^2$ external heat exchanger with pump round loop. The coolant was glycol/water cooled via a 5 kilowatt refrigerator. This was set to nominally provide $-18°$ C. coolant, but in practice could only reach $-15°$ C. due to heat losses. Phosphorus trichloride (50.2 moles) was then added in less than 5 minutes. Tripropylamine (154 moles) was charged over 2 hours. This maintained the temperature of the reaction mixture in the range of $-6°$ C. to $-10°$ C. The mixture remained easily stirrable throughout the addition. There was no observable coating of the reactor walls by the mixture.

This was repeated a further four times without any noticeable interference with regards to stirring. No fouling of the heat exchanger system was observed.

It is clear from the foregoing examples that carrying out the method of the present invention avoids the disadvantages of previous methods. In particular, the reaction produces a slurry which is pumpable, stirrable and operable at scale. Indeed, the fluidity of the reaction system allows the process to operate more concentrated than previous methods.

What is claimed is:

1. In a method for the production of an aromatic phosphite by reacting an aromatic hydroxy-compound with a phosphorus trihalide in the presence of a tertiary amine and a non-protic solvent, said solvent being mobile below $-20°$ C., the improvement comprising the use, as said tertiary amine, of a tertiary amine selected from the group consisting of tri-propyl amines and tri-butyl amines.

2. A method according to claim 1, in which said amine is selected from the group consisting of tri-n-propylamine and tri-iso-propylamine.

3. A method according to claim 1, in which said amine is selected from the group consisting of tri-n-butylamine, tri-iso-butylamine and tri-t-butylamine.

4. A method according to claim 1, in which said phosphorus trihalide is selected from the group consisting of phosphorus trichloride and phosphorus tribromide.

5. A method according to claim 1, in which said aromatic hydroxy-compound is selected from the group consisting of substituted aromatic mono-hydric alcohols, substituted aromatic poly-hydric alcohols, unsubstituted aromatic mono-hydric alcohols, unsubstituted aromatic poly-hydric alcohols, substituted diphenols, unsubstituted diphenols, substituted resorcinols, unsubstituted resorcinol, substituted quinones and unsubstituted quinone.

6. A method according to claim 5, in which said aromatic hydroxy-compound is thymol.

7. A method according to claim 1, in which said aromatic hydroxy-compound has a condensed ring system.

8. A method according to claim 7, in which said aromatic hydroxy-compound is selected from the group consisting of substituted mono-hydric naphthols, substituted mono-hydric anthrols, substituted mono-hydric phenanthrols, unsubstituted mono-hydric naphthols, unsubstituted mono-hydric anthrols, unsubstituted mono-hydric phenanthrols, substituted poly-hydric naphthols, substituted poly-hydric anthrols, substituted poly-hydric phenanthrols, unsubstituted poly-hydric naphthols, unsubstituted poly-hydric anthrols and unsubstituted poly-hydric phenanthrols.

9. A method according to claim 1, in which said solvent is selected from the group consisting of toluene, xylene, monochlorobenzene, dichlorobenzene and 1, 4, 5,-trimethyl benzene.

* * * * *